United States Patent [19]

Körösi et al.

[11] Patent Number: 4,835,152
[45] Date of Patent: May 30, 1989

[54] 1-(4-AMINOPHENYL)-4-METHYL-7,8-METHYLENEDIOXY-3,4-DIHYDRO-5H-2,3-BENZODIAZEPINE AND ACID ADDITION SALTS THEREOF SAME

[75] Inventors: Jenő Kőrösi; Tibor Láng; Ferenc Andrási; Pál Berzsenyi; Péter Botka; Tamás Hámori; Katalin G. Horváth; József Borsi; István Elekes; Zsuzsanna L. Rihmer, all of Budapest, Hungary

[73] Assignee: Biogal Gyogyszergyar, Debrecen, Hungary

[21] Appl. No.: 87,341

[22] Filed: Aug. 20, 1987

[30] Foreign Application Priority Data

Aug. 15, 1986 [HU] Hungary .............................. 3594/86

[51] Int. Cl.⁴ ................. C07D 491/056; A61K 31/55
[52] U.S. Cl. ..................................... 514/220; 540/557
[58] Field of Search ............... 540/557, 567; 514/220, 514/221

[56] References Cited

U.S. PATENT DOCUMENTS 4,423,044 12/1983 Korosi et al. ..................... 514/220
4,514,740 9/1986 Lang ................................ 514/221

Primary Examiner—Robert Gerstl
Attorney, Agent, or Firm—Keil & Winkauf

[57] ABSTRACT

The invention relates to new 1-(4-aminophenyl)-4-methyl-7,8-methylenedioxy-3,4-dihydro-5H-2,3-benzodiazepine of formula (I), optically active isomers and acid addition salts thereof as well as to pharmaceutical compositions containing these compounds.

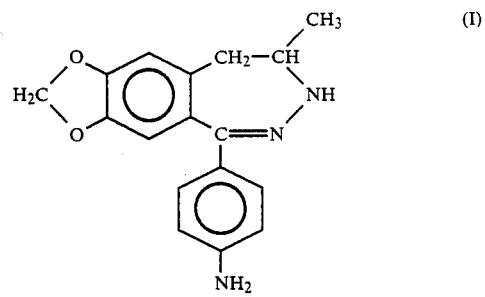

The new compounds of formula (I) can be prepared by reducing 1-(4-aminophenyl)-4-methyl-7,8-methylenedioxy-5H-2,3-benzodiazepine of formula (II) with an inorganic or organic-inorganic and/or complex metal hydride and, if desired, separating the optically active forms of the compound of formula (I) thus-obtained and, if desired, converting the base or bases into acid addition salts or converting the salts into the free base(s).

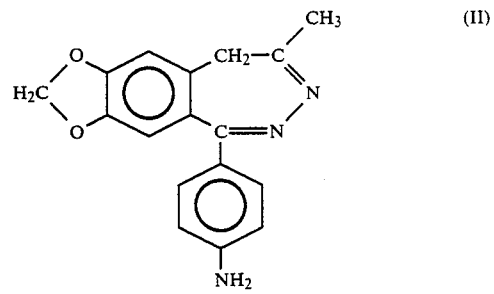

The new compound of formula (I) possesses significant central nervous effects and can advantageously be used in the therapy.

7 Claims, No Drawings

1-(4-AMINOPHENYL)-4-METHYL-7,8-METHYLENEDIOXY-3,4-DIHYDRO-5H-2,3-BENZODIAZEPINE AND ACID ADDITION SALTS THEREOF SAME

The invention relates to new, therapeutically useful 1-(4-aminophenyl)-4-methyl-7,8-methylenedioxy-3,4-dihydro-5H-2,3-benzodiazepine of formula (I), optically active isomers and acid addition salts thereof as well as to pharmaceutical compositions containing the same. Further on, the invention relates to processes for preparing the abovementioned new compounds and pharmaceutical compositions containing the same.

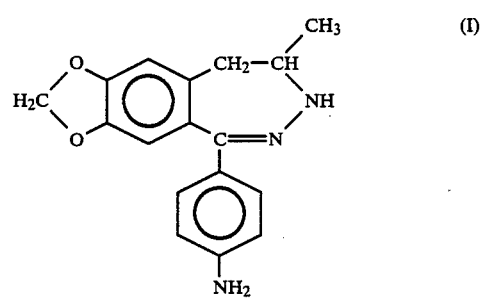

The compound of formula (I) of the invention and acid addition salts thereof show valuable pharmacodynamic effect, they possess CNS stimulating activity.

Some 3,4-dihydro-5H-2,3-benzodiazepines, the structures of which are different from that of the compound of the invention and which contain alkoxy group(s) in positions 7 and 8, and no substituent in position 1 of the benzodiazepine nucleus, are known in the literature [see e.g. Chem. Ber. 95, 2012 (1962); Synthesis 1973, 159 and 1977, 1; Helv. Chim. Acta 59, 2786 (1976)]. No data were published on the biological activity of these substances. Other 3,4-dihydro-5H-2,3-benzodiazepines with an alkyl, cycloalkyl, phenyl or substituted phenyl group in position 1 and alkoxy group(s) in positions 7 and 8 of the benzodiazepine nucleus are also known in the literature. These compounds possess spontaneous motor activity decreasing, narcosis potentiating and mild CNS depressant effects (published German patent application No. 3,209,100).

The present invention is based on the unexpected finding that, unlike the known 3,4-dihydro-5H-2,3-benzodiazepine derivatives and even all the 5H-2,3-benzodiazepines known so far, the compound of formula (I) of the invention and acid addition salts thereof are of CNS stimulating character showing an effect that is entirely new among benzodiazepines.

To some extent, the pharmacological range of effects of the compound is similar to that of dopamine-agonists, increasing spontaneous motor activity, causing stereotypy and antagonizing the effect of dopamine receptor blocking neuroleptics (chlorpromazine, haloperidol, etc.). However, unlike known dopamine agonists (apomorphine, bromocriptine) they do not show emetic side-effect. Besides, the compounds also exert a strong inhibitory effect on the tremor elicited by oxotremorine.

Considering the fact that influencing dopaminergic mechanisms results in the modification of several functions of the nervous system (co-ordinated muscle contraction, learning processes, regulation of the blood pressure and the endocrine system), the therapeutic use of the compounds of the invention is expected to be for one of the diseases related to these functions (e.g. Parkinson's disease).

According to the invention, the compound of formula (I) and acid addition salts thereof are prepared by reducing the 1-(4-aminophenyl)-4-methyl-7,8-methylenedioxy-5H-2,3-benzodiazepine of formula (II) in a suitable solvent with an inorganic or inorganic-organic hydride and/or complex metal hydride and, if desired, separating optically active forms of the compound of formula (I) thus-obtained and, if desired, converting the base or bases into acid addition salts, or converting the salt into a free base.

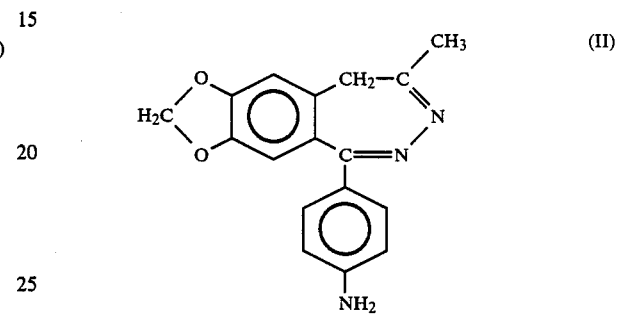

The selective reduction of the compound of formula (II) can be preferably carried out with the following known hydrides and complex metal hydrides: sodium hydride, lithium hydride, calcium hydride, diborane, silane, diethyl silane, lithium aluminium hydride, sodium borohydride, potassium borohydride, sodium borohydride-aluminium chloride, sodium dihydro-bis-(2-methoxy-ethoxy)-aluminate, sodium cyanoborohydride, lithium trimethoxy-aluminium hydride or sodium borohydride-triethyloxonium fluoroborate.

The reduction is preferably carried out in the following solvents or solvent mixtures: water, ethers, alcohols, primary amines, aromatic hydrocarbons, chlorinated aliphatic hydrocarbons, aliphatic carboxylic acids and pyridine. The reaction medium actually used depends on the reducing agent applied. It is preferable to carry out the reduction in a solvent mixture that does not react (or only very slowly) with the reducing agent used. On carrying out the process of the invention the preferred solvent is pyridine.

The reduction is preferably carried out at a temperature between 50° C. and 110° C.

Our experiments show that the reducing agent is to be used in an excess of 300 to 500% for the complete reduction of the compound of formula (II), as the compound to be reduced also has an amino group that binds some of the reducing agent.

On carrying out the process of the invention, the aimed compound is obtained as a free base. The pharmaceutically acceptable acid addition salts of the base of formula (I) are formed in a known way: the base is dissolved or suspended in an appropriate solvent, e.g. in water, methanol, ethanol, isopropanol or ethylacetate and then an appropriate acid or a suitable solution of the acid is added. It is preferable to use a non-toxic, inorganic acid such as hydrochloric, hydrobromic, sulfuric, phosphoric acid or a non-toxic organic acid such as acetic acid, tartaric acid, methanesulfonic acid, maleic acid, fumaric acid, etc. The salts are isolated either by filtration or by evaporating the solvent. If desired, the thus-obtained product is suspended, recrystallized and/or dried under reduced pressure.

The carbon atom in position 4 of 1-(4-aminophenyl)-4-methyl-7,8-methylenedioxy-3,4-dihydro-5H-2,3-benzodiazepine of formula (I) is asymmetric, thus the compound can be treated, if desired, to separate the individual isomers from each other by conventional methods, e.g. by forming a diastereomeric pair of salts. For this purpose an optically active acid, e.g. D-10-camphorsulfonic acid, is used.

The preparation of the starting substance of the process of the invention [1-(4-aminophenyl)-4-methyl-7,8-methylenedioxy-5H-2,3-benzodiazepine of formula (II)] is described in the literature (published German patent application No. 3,527,117).

As it was mentioned above, the compound of formula (I) of the invention and acid addition salts thereof show valuable CNS stimulating activity. The pharmacological effects of the compounds are presented for the 1-(4-aminophenyl)-4-methyl-7,8-methylenedioxy-3,4-dihydro-5H-2,3-benzodiazepine base as an example (Example 1).

1.a. Motility studies on mice

For studying how the compound prepared according to Example 1 increases the motility in male mice, two-hour experiments were carried out. In order to determine the spontaneous motor activity, the component of hunger-activity was excluded (the mice were not fasted), thus only the exploratory activity was recorded. The test animals were placed into the observation box immediately after the intraperitoneal treatment. The data obtained are shown in Table 1.

TABLE 1

| Dose mg/kg i.p. | Number of animals | Increase in motility % |
|---|---|---|
| 3 | 27 | 15 |
| 10 | 21 | 131 |
| 30 | 18 | 473 |

1.b. Motility studies on rats

Male CFY rats weighing 120 to 140 g were treated intraperitoneally in groups of three with a dose of 10, 20, 25 or 30 mg/kg of the compound of Example 1, and were immediately placed into the observation box. The experiment lasted for 2 hours. The results obtained are shown in Table 2.

TABLE 2

| Dose mg/kg i.p. | Number of animals | Increase in motility % |
|---|---|---|
| 10 | 18 | 21 |
| 20 | 18 | 87 |
| 25 | 18 | 106 |
| 30 | 18 | 462 |

The data of Tables 1 and 2 demonstrate that the compound of the invention increases the motility or spontaneous motor activity of mice and rats in a dose-dependent manner.

2. Measurement of the haloperidol-antagonistic effect in mice

Male CFLP mice weighing 20 to 22 g were treated intraperitoneally with a dose of 0.5 mg/kg of 4-[4-(4-chlorophenyl)-4-hydroxy-1-piperidinyl]-1-(4-fluorophenyl)-1-butanone (haloperidol) and the spontaneous motor activity (SMA) was measured, in relation to the data obtained in the controls, by a capacitance-sensitive motimeter. Another group of the test animals was treated also with a dose of 30 mg/kg of the compound of Example 1, 15 minutes after the administration of haloperidol. The haloperidol-induced decrease in SMA was significantly antagonized by the compound of Example 1. The results are summarized in Table 3.

TABLE 3

| Compound | Dose mg/kg i.p. | Number of animals | Decrease in SMA % |
|---|---|---|---|
| Haloperidol | 0.5 | 24 | 62.6 |
| Haloperidol + the compound of Example 1 | 0.5 30 | 24 | 17.1 |

3. Examination of stereotypy in rats

For the measurement of stereotypy the method of B. Costall and R. I. Naylor [Eur. J. Pharmacol. 18, 95 (1972)] was used. The score values in Table 4 are average score values obtained at the time of reading. The results are shown in Table 4.

TABLE 4

| Dose mg/kg | | Number of animals | Time (min) | | | | | | |
|---|---|---|---|---|---|---|---|---|---|
| | | | 15 | 30 | 60 | 90 | 120 | 180 | 240 |
| Compound of Example 1 | | | | | | | | | |
| 3.125 | i.p. | 10 | 0.3 | 0.3 | 0.1 | 0 | 0 | 0 | 0 |
| 6.25 | i.p. | 10 | 1.0 | 1.3 | 0.3 | 0 | 0 | 0 | 0 |
| 12.5 | i.p. | 10 | 1.2 | 1.3 | 1.1 | 1.0 | 0 | 0 | 0 |
| 25.0 | i.p. | 20 | 1.3 | 1.5 | 1.8 | 1.6 | 1.0 | 0.8 | 0.4 |
| 50.0 | i.p. | 15 | 1.5 | 2.1 | 2.7 | 2.4 | 2.4 | 1.7 | 0.6 |
| 6.25 | p.o. | 10 | 0.7 | 0.7 | 0.6 | 0 | 0 | 0 | 0 |
| 12.5 | p.o. | 10 | 0.4 | 0.9 | 1.4 | 0.4 | 0 | 0 | 0 |
| 25.0 | p.o. | 10 | 0.7 | 1.1 | 1.5 | 0.6 | 0.6 | 0.3 | 0 |
| 50.0 | p.o. | 10 | 1.7 | 1.9 | 2.3 | 2.3 | 1.9 | 1.1 | 0.2 |
| Bromocriptine | | | | | | | | | |
| 5 | i.p. | 6 | | 0.2 | 0.6 | | 0.8 | 1.1 | 0.4 |
| 10 | i.p. | 6 | | 0.5 | 1.0 | | 1.8 | 1.9 | 1.5 |
| 20 | i.p. | 6 | | 0.6 | 1.2 | | 2.2 | 2.4 | 1.8 |

Like bromocriptine, the compound of Example 1 causes stereotypy. This effect develops earlier but it is somewhat weaker than the effect of bromocriptine.

4. Inhibition of oxotremorine in mice

The examinations were carried out according to the method of R. C. Rathbun and I. H. Slater [Psychopharm. 4, 114 (1963)]. One hour after male, starving CFLP mice were orally pre-treated with a dose of 6.25, 12.5 or 25.0 mg/kg of the compound of Example 1, they were intraperitoneally treated with a dose of 1 mg/kg of 1-[4-(1-pyrrolidinyl)-2-butinyl]-2-pyrrolidinone (oxotremorine).

The inhibition of oxotremorine-induced tremor and salivation exerted by the compound of Example 1 was measured in relation to the control group treated with oxotremorine only. The strength of the inhibition was expressed in scores (0, 0.5, 1, 2 or 3). The results are shown in Table 5.

TABLE 5

| Dose mg/kg p.o. | Number of animals | Inhibition in relation to control group (%) | $ED_{50}$ mg/kg p.o. |
|---|---|---|---|
| 6.25 | 15 | 17 | |

TABLE 5-continued

| Dose mg/kg p.o. | Number of animals | Inhibition in relation to control group (%) | $ED_{50}$ mg/kg p.o. |
|---|---|---|---|
| 12.5 | 15 | 50 | 13.5 |
| 25.0 | 15 | 74 | (9.5–19.1) |

The compound of Example 1 does not inhibit the oxotremorine-induced salivation, however, it significantly decreases the tremor.

5. Dependence studies

The examinations were carried out using the DAF (drug admixed food) method [E. Tagashira et al. Psychopharmacologia 57, 137–144 (1978)]. Male CFY rats (number of animals 24) were fed for 6 weeks with a rat chaw containing 0.05% (w/w) of the compound of Example 1. The average daily dose of the active agent was 40 mg/kg, 5 to 10-fold of the therapeutic dose. The body weight, food consumption, motility, body temperature and behaviour of the animals were examined. These examinations were continued for two weeks after the withdrawal of the active agent. Withdrawal symptoms or signs of dependence were not observed during the examinations, in contrast with psychostimulants of the amphetamine type.

6. Toxicity data

The acute toxicity values ($LD_{50}$) of the compound of Example 1:

| in mice | 260 mg/kg | i.p. |
|---|---|---|
| | 300 mg/kg | p.o. |
| in rats | 250 mg/kg | i.p. |
| | 350 mg/kg | p.o. |

The pharmacological data obtained clearly demonstrate that the compound of the invention possesses the character of a psychostimulant and dopamine agonist, in contrast with 5H-2,3-benzodiazepines and 3,4-dihydro derivatives thereof described in the literature so far, which are mainly CNS depressants. As a further feature, the compound does not have the unfavourable side-effects of the known psychostimulants (emetic effect, proneness to dependence).

Based on the results of the pharmacological studies the compound of formula (I) of the invention and acid addition salts thereof have therapeutic importance in the treatment of diseases related to the functional disorders of the dopaminergic systems (e.g. Parkinson's disease, galactorrhoea, etc.). The valuable pharmacological properties and low toxicity together provide an advantageous therapeutic safety and range of effects.

For therapeutic purposes, the daily dose of the active agents of the invention amounts commonly to 0.5 to 4.0 mg/kg of body-weight, preferably to 1.0 to 2.0 mg/kg of body-weight, which is administered daily, optionally divided into several doses with consideration of the absorption conditions.

For therapeutic use, the active compounds of the invention are suitably formulated to pharmaceutical compositions by mixing them with the commonly used, non-toxic, inert, solid or liquid pharmaceutical carriers and/or auxiliary materials useful for enteral or parenteral administration. As carriers, e.g. water, gelatine, lactose, starch, cellulose, pectin, magnesium stearate, stearic acid, talc or vegetable oils can be used. As auxiliary materials, e.g. preservatives and wetting as well as emulsifying, dispersing and aromatizing agents and buffers can be employed.

By using the above-mentioned carriers and auxiliary materials, the active agents of the invention can be transformed to useful pharmaceutical compositions, e.g. to solid compositions (such as tablets, capsules, pills or suppositories) or liquid compositions (such as aqueous or oily solutions, suspensions, emulsions or syrups) as well as to injectable solutions, suspensions or emulsions.

The process of the invention is illustrated in detail by the aid of the following non-limiting Examples. The compounds prepared were identified by elementary analysis, IR, $^1$H-NMR and/or mass spectrometry.

EXAMPLE 1

Preparation of 1-(4-aminophenyl)-4-methyl-7,8-methylenedioxy-3,4-dihydro-5H-2,3-benzodiazepine A mixture of 8.80 g (0.03 moles) of 1-(4-aminophenyl)-4-methyl-7,8-methylenedioxy-5H-2,3-benzodiazepine, 5.675 g (0.15 moles) of sodium borohydride and 80 ml of pyridine is stirred on a water bath heated to boiling, for 5 hours. When the reaction mixture is cool, 90 ml of water is added to it, then, under ice-cooling, 260 ml of an aqueous hydrochloric acid solution containing 110 ml of concentrated hydrochloric acid are added, and thereafter 115 ml of 40% aqueous sodium hydroxide solution are dropped to the reaction mixture. On adding the water, hydrogen evolution occurs, on adding the base the aimed compound separates in the form of an oil containing pyridine. The mixture is then extracted with benzene, the benzene phase is shaken with water, dried, clarified with activated charcoal and evaporated under reduced pressure. The residue is taken up in 50 ml of water, the crude product is filtered off, washed 5 times with 10 ml of water, dried at 50°–60° C., recrystallized from 16 ml of 50% aqueous ethanol and finally the crystal water is removed at 100°–105° C. under reduced pressure.

Yield: 6.3 g (71.1%), m.p.: 118°–120° C.

Elementary analysis, calculated for the molecular formula $C_{17}H_{17}N_3O_2$; m.w.: 295.347, Found: C 68.98%, H 5.96%, N 14.15%, Calculated: C 69.13%, H 5.80%, N 14.23%.

EXAMPLE 2

Preparation of 1-(4-aminophenyl)-4-methyl-7,8-methylenedioxy-3,4-dihydro-5H-2,3-benzodiazepine dihydrochloride 2.95 g (0.01 mole) of 1-(4-aminophenyl)-4-methyl-7,8-methylenedioxy-3,4-dihydro-5H-2,3-benzodiazepine is dissolved in 50 ml of 99.5% ethanol heated to boiling, then 1.77 ml (0.022 moles) of concentrated hydrochloric acid and 50 ml of benzene are added, and the solvent of the yellow reaction mixture is evaporated under reduced pressure. The residue is taken up in 20 ml of isopropanol, filtered off and dried at 60°–80° C. the crude product (3.7 g; decomposing and getting charred over 223° C.) is suspended in 30 ml of isopropanol heated to boiling (part of the product dissolves), after cooling the fine crystals are filtered off, washed and dried at 100°–120° C.

Yield: 3.4 g (92.3%), m.p.: decomposes and gets charred over 227° C.

Mass spectrum: m/z=295 (M+·, 100%), 252 (90), 253 (37), 280 (32.7), 160 (31), 294 (16), 118 (10.5)

Elementary analysis, calculated for the molecular formula $C_{17}H_{17}N_3O_2.2HCl$; m.w.: 368.277.

Found: C 19.09%, N 11.33%, Calculated: C 19.26%, N 11.41%.

EXAMPLE 3

Preparation of 1-(4-aminophenyl)-4-methyl-7,8-methylenedioxy-3,4-dihydro-5H-2,3-benzodiazepine methanesulfonate This compound was prepared according to the method described in Example 2, with methanesulfonic acid.

M.p.: 215°–217° C. (decomposes).

According to the IR and NMR spectra the proton is bound to the N atom in position 3 of the 7-membered ring.

Elementary analysis calculated for the molecular formula $C_{17}H_{17}N_3O_2.CH_3SO_3H$, m.w.: 392.464.

Found: C 55.22%, H 5.64%, S 8.29%, Calculated: C 55.09%, H 5.39%, S 8.17%.

EXAMPLE 4

Preparation of pharmaceutical compositions (A.) Tablets containing 25 mg of 1-(4-aminophenyl)-4-methyl-7,8-methylenedioxy-3,4-dihydro-5H-2,3-benzodiazepine of Example 1 are prepared in a manner known per se. The composition of one tablet is as follows:

| | |
|---|---|
| Active ingredient | 25.0 mg |
| Magnesium stearate | 0.5 mg |
| Stearin | 0.5 mg |
| Talc | 1.0 mg |
| Gelatine | 1.7 mg |
| Cellulose /micro crystals/ | 5.0 mg |
| Maize starch | 10.3 mg |
| Lactose | 46.0 mg |
| | 90.0 mg |

(B.) Dragées containing 25 mg of 1-(4-aminophenyl)-4-methyl-7,8-methylenedioxy-3,4-dihydro-5H-2,3-benzodiazepine of Example 1 are prepared in a manner known per se. The composition of one dragée kernel is as follows:

| | |
|---|---|
| Active ingredient | 25.0 mg |
| Magnesium stearate | 1.0 mg |
| Polivinyl pyrrolidone | 5.0 mg |
| Maize starch | 16.0 mg |
| Lactose | 38.0 mg |
| | 85.0 mg |

The dragée kernels are coated in the usual way, by a layer containing sugar and talc, and finally polished using beewax. The weight of a finished dragée is about 120 mg.

What we claim is:

1. 1-(4-Aminophenyl)-4-methyl-7,8-methylenedioxy-3,4-dihydro-5H-2,3-benzodiazepine, optically active forms and racemates thereof as well as acid addition salts of these compounds.

2. 1-(4-Aminophenyl)-4-methyl-7,8-methylenedioxy-3,4-dihydro-5H-2,3-benzodiazepine.

3. 1-(4-Aminophenyl)-4-methyl-7,8-methylenedioxy-3,4-dihydro-5H-2,3-benzodiazepine dihydrochloride.

4. 1-(4-Aminophenyl)-4-methyl-7,8-methylenedioxy-3,4-dihydro-5H-2,3-benzodiazepine methanesulfonate.

5. A pharmaceutical composition with a CNS stimulating effect containing as active ingredient at least one compound of formula (I)

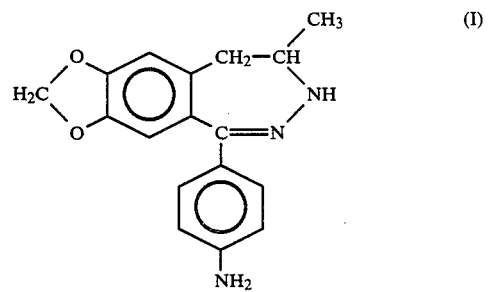

or a pharmaceutically acceptable acid addition salt thereof, together with a conventional inert, non-toxic, solid or liquid carrier and/or additive.

6. Method for treating the disorders of the dopaminergic system, whcih comprises administering to the patient either enterally or parenterally an effective amount of the composition of claim 5.

7. The method of claim 6, wherein the composition is employed in a daily dosage amount of 1 to 2 mg/kg of body-weight.

* * * * *